(12) United States Patent
Kim

(10) Patent No.: US 10,231,845 B2
(45) Date of Patent: Mar. 19, 2019

(54) CAGE APPARATUS FOR MINIMAL INVASIVE SURGERY

(71) Applicant: MEDRICS CO., LTD., Seoul (KR)

(72) Inventor: Jin Sung Kim, Yongin-si (KR)

(73) Assignee: MEDRICS CO., LTD., Seoul (KR)

( * ) Notice: Subject to any disclaimer, the term of this patent is extended or adjusted under 35 U.S.C. 154(b) by 205 days.

(21) Appl. No.: 15/324,568

(22) PCT Filed: Jul. 6, 2016

(86) PCT No.: PCT/KR2016/007340
§ 371 (c)(1),
(2) Date: Jan. 6, 2017

(87) PCT Pub. No.: WO2017/010734
PCT Pub. Date: Jan. 19, 2017

(65) Prior Publication Data
US 2017/0196698 A1    Jul. 13, 2017

(30) Foreign Application Priority Data

Jul. 10, 2015    (KR) ......................... 10-2015-0098093

(51) Int. Cl.
*A61F 2/44*    (2006.01)
*A61F 2/30*    (2006.01)

(52) U.S. Cl.
CPC .......... *A61F 2/447* (2013.01); *A61F 2/30771* (2013.01); *A61F 2/4455* (2013.01); *A61F 2002/30383* (2013.01); *A61F 2002/30395* (2013.01); *A61F 2002/30398* (2013.01); *A61F 2002/30401* (2013.01); *A61F 2002/30482* (2013.01); *A61F 2002/30538* (2013.01); *A61F 2002/30556* (2013.01);
(Continued)

(58) Field of Classification Search
CPC ...... A61F 2/4455; A61F 2/446; A61F 2/4465; A61F 2/447
USPC ............................................ 623/17.15, 17.16
See application file for complete search history.

(56) References Cited

U.S. PATENT DOCUMENTS

| 7,094,257 | B2 | 8/2006 | Mujwid et al. |
| 8,628,578 | B2 | 1/2014 | Miller et al. |
| 2013/0158667 | A1* | 6/2013 | Tabor .................... A61F 2/4455 |
| | | | 623/17.16 |

FOREIGN PATENT DOCUMENTS

| KR | 10-2006-0113640 A | 11/2006 |
| KR | 10-2013-0082281 A | 7/2013 |
| KR | 10-1371418 B1 | 3/2014 |

* cited by examiner

*Primary Examiner* — Si Ming Ku
(74) *Attorney, Agent, or Firm* — Novick, Kim & Lee, PLLC; Jae Youn Kim

(57) ABSTRACT

The present invention relates to a cage apparatus for minimal invasive surgery. The cage apparatus includes: a first main body inserted between a first vertebra and a second vertebra adjacent to the first vertebra; a second main body inserted between the first vertebra and the second vertebra to face the first main body; a torsion prevention unit fixed to each of both edges of each of the first and second main bodies and disposed between the first and second main bodies; and a locking unit forwardly/reversely rotatably mounted between the first and second main bodies to suppress movement of the torsion prevention unit between the first and second main bodies. Thus, when the surgery is performed, the cage apparatus may be easily inserted between a vertebra and an adjacent vertebra to previously prevent damage due to torsion from occurring.

6 Claims, 5 Drawing Sheets

(a)

(b)

(52) U.S. Cl.
CPC ............... *A61F 2002/30828* (2013.01); *A61F 2002/30836* (2013.01); *A61F 2002/30843* (2013.01); *A61F 2002/30879* (2013.01); *A61F 2002/30904* (2013.01); *A61F 2002/4475* (2013.01)

CAGE APPARATUS FOR MINIMAL INVASIVE SURGERY

TECHNICAL FIELD

The present invention relates to a cage apparatus for minimal invasive surgery, and more particularly, to a cage apparatus for minimal invasive surgery, which is capable being easily inserted between a vertebra and an adjacent vertebra to previously prevent damage due to torsion from occurring.

BACKGROUND ART

Generally, in case of existing laparotomy surgery for the treatment of patients, since an incision site is large, and an amount of blood loss during the surgery is large, recovery of a patient is slow. In addition, a large scar remains after the surgery to negatively affect patient's lives in the past.

To overcome the above-described disadvantages of the laparotomy surgery, novel surgical techniques such as minimal invasive surgery (MIS) using a laparoscopic surgical instrument are being developed in recent years.

The MIS may be a surgical technique in which a thin and long surgical instrument that is specifically designed to minimize an incision site required for the surgery is used to incise only a minimal part in the body surface of the patient.

Since the incision site required for the surgery is small, and the amount of blood loss during the surgery is small in the MIS compared to that of the laparotomy surgery, the recovery of the patent is fast, an external visible scar is small. As a result, the number of MIS is being remarkably increasing in recent years.

A disc existing between vertebrae functions as a joint and plays very important roles for minimizing an impact applied to the vertebrae while vertebral pulp accommodated inside the disc changes in position and shape according to the movement of the vertebrae.

The vertebral pulp is mostly moisture (water). When we get older, an amount of moisture gradually decreases, and thus, a buffer function of a disc is lost.

As a result, when an excessive pressure is applied to the fibers, backache may occur. Here, if the excessive pressure is continuously applied, the fibers may be seriously stretched or ruptured to push nerve roots placed at a rear side thereof, thereby causing pains of pelvis, legs, and the like.

Thereafter, a distance between the vertebrae gradually decreases, or the vertebrae are collapsed to cause various kinds of side effects such as vertebral deformation.

There is a method, in which an intervertebral fusion device, so-called, a cage is inserted between two adjacent vertebrae after a disc between the damaged vertebrae is removed, as a method for treating diseases involved due to the disc.

That is, the cage recovers the distance between the vertebrae to its original distance between the two adjacent vertebrae, which corresponds to an original height of the disc, thereby recovering the vertebral function.

The surgical method in which the cage is inserted between the vertebrae includes an anterior lumbar interbody fusion (ALIF) method in which a cage is inserted from a front side of a vertebra after an abdominal operation, a lateral lumbar interbody fusion (LLIF) method in which a cage is inserted through a side portion, a transforaminal lumbar interbody fusion (TLIF) method in which a cage is inserted in a diagonal direction at a point that is spaced a distance of 30 mm to 40 mm laterally from a center of a back, a posterior lumbar interbody fusion (PLIF) method in which a cage is inserted from a back, and the like.

For example, there is an "intervertebral fusion device" (hereinafter, referred to as a 'prior art') disclosed in Korean Patent Registration No. 10-1371418.

The prior art has a structure including: a vertical rear part; top and bottom surfaces respectively integrated with upper and lower portions of the rear part to face each other and extending to be gradually widened forward from the rear part; a top surface front part having a curvature that is convexly curved from an extension end of the top surface to the bottom surface; a bottom surface front part having a curvature that is convexly curved from an extension end of the bottom surface to the top surface; and a through-hole for synostosis of the top and bottom surfaces.

However, most cages according to the prior art are vulnerable to torsion stress applied between the top and bottom surfaces and the rear part when a subject person perform motion such as twisting of his/her waist after the surgery. Also, when the cages are used for a long time, the cages are faced with a fatal problem such as breakage of the connection portion.

Also, in the most cages according to the prior art, when each of the cages is inserted between a vertebra and an adjacent vertebra during the surgery, since a front end of the cage does not have a sharp shape, tissues such as blood vessels or nerves may be damaged while the cage is inserted through an opening of the subject person.

Thus, the damage due to the torsion stress may act as a factor that causes pain of the patient again. As a result, it is highly likely that the patient has to re-operate and thus suffers pain again.

DISCLOSURE OF THE INVENTION

Technical Problem

To improve the above-mentioned problems, an object of the present invention is to provide a cage apparatus for minimal invasive surgery, which is capable being easily inserted between a vertebra and an adjacent vertebra during the surgery to previously prevent damage due to torsion from occurring.

Also, another object of the present invention is to provide a cage apparatus for minimal invasive surgery, which is capable of forming a minimal opening in the body of a subject person to enable the minimal invasive surgery, thereby reducing pain the subject person and promote recovery of a subject person.

Technical Solution

To achieve the above-described objects, a cage apparatus for minimal invasive surgery includes: a first main body inserted between a first vertebra and a second vertebra adjacent to the first vertebra; a second main body inserted between the first vertebra and the second vertebra to face the first main body; a torsion prevention unit fixed to each of both edges of each of the first and second main bodies and disposed between the first and second main bodies; and a locking unit forwardly/reversely rotatably mounted between the first and second main bodies to suppress movement of the torsion prevention unit between the first and second main bodies.

Here, the cage apparatus may further include a first spacing protrusion piece protruding from each of both sides of a rear bottom surface of the first main body; and a second spacing protrusion piece protruding from each of both sides of a rear top surface of the second main body to contact the first spacing protrusion piece, wherein, in a state in which the first and second spacing protrusion pieces contact each other to form an inclination that is gradually narrowed forward from a rear side of each of the first and second main bodies, a front end of the torsion prevention unit may be guided to be inserted and coupled between the rear bottom surface of the first main body and the rear top surface of the second main body.

Here, the first main body may include: a first outer frame in which a first operation through-hole having a predetermined length and width is defined and having four sides; a first front hook rib protruding from a right edge of the first operation through-hole in a left direction; a first rear hook rib protruding from a left edge of the first operation through-hole in a right direction and disposed at a rear side of the first front hook rib; a first coupling groove defined in a rear end of the first outer frame and disposed on a bottom surface of the first outer frame, the first coupling groove being recessed in a circular arc shape and coupled to the lock unit; and a first operation stepped groove recessed from a side surface of the rear end of the first outer frame and into which a rear end of the locking unit is accommodated, wherein the bottom surface of the first outer frame may face a top surface of the second main body, and both sides of the torsion prevention unit may be coupled along both left and right bottom surfaces of the first outer frame, respectively.

Also, the second main body may include: a second outer frame in which a second operation through-hole having a predetermined length and width is defined and having four sides; a second front hook rib protruding from a left edge of the second operation through-hole in a right direction; a second rear hook rib protruding from a right edge of the second operation through-hole in a left direction and disposed at a rear side of the second front hook rib; a second coupling groove defined in a rear end of the second outer frame and disposed on a top surface of the second outer frame, the second coupling groove being recessed in a circular arc shape and coupled to the lock unit; and a second operation stepped groove recessed from a side surface of the rear end of the second outer frame and into which a rear end of the locking unit is accommodated, wherein the top surface of the second outer frame may face a bottom surface of the first main body, and both sides of the torsion prevention unit may be coupled along both left and right top surfaces of the second outer frame, respectively.

Also, the torsion prevention unit may include: a protection guide ring having a ring shape and accommodated into each of a first operation stepped groove recessed from a rear outer surface of the first main body and a second operation stepped groove recessed from a rear outer surface of the second main body; a pair of coupling ribs extending from both sides of an outer circumferential surface of the protection guide ring to parallel to each other and respectively coupled to left and right bottom surfaces of the first main body and left and right top surfaces of the second main body; a main guide rib extending along the formation direction of each of the pair of coupling ribs to protrude from top and bottom surfaces of each of the pair of coupling ribs; and an auxiliary guide protrusion piece protruding from each of both ends of the main guide rib along the formation direction of the main guide rib, wherein a rear end of the locking unit may be forwardly/reversely rotatably accommodated into an inner space of the protection guide ring, and a front end of the locking unit may be detachably coupled to inner surfaces of the pair of coupling ribs facing each other, and a coupling structure having a space corresponding to that of each of the main guide rib and the auxiliary guide protrusion piece may be disposed on each of left and right bottom surfaces of the first main body and left and right top surfaces of the second main body.

Also, the locking unit may include: a rotatable body which has a cylindrical shape and is forwardly/reversely rotatably coupled and of which an outer circumferential surface contacts a first coupling groove defined in a rear bottom surface of the first main body and a second coupling groove defined in a rear top surface of the second main body; detachable wings detachably coupled to left and right inner surfaces of the torsion prevention unit coupled and disposed between the first and second main bodies while respectively extending from both side of an outer circumferential surface of a front end of the rotatable body and being interlocked with the rotatable body so as to be forwardly/backwardly rotatable; and control wings maintaining or releasing the coupled state of the detachable wings with respect to the torsion prevention unit while respectively extending from both sides of a rear end of the rotatable body and being interlocked with the rotatable body so as to be forwardly/backwardly rotatable.

Also, the cage may further include: a front band made of an elastic material and fixing a first front hook rib disposed on a front side of the first main body and a second front hook rib disposed on a front side of the second main body to mutually face-to-face contact the first front hook rib at the same time; and a rear band made of an elastic material and fixing a first rear hook rib disposed on a rear side of the first main body and a second rear hook rib disposed on a rear side of the second main body to mutually face-to-face contact the first rear hook rib at the same time.

Advantageous Effects

According to the foregoing embodiments, the following effects may be attained.

First, according to the present invention, the structure in which the torsion prevention unit is coupled between the first and second main bodies, and the locking unit maintains the coupled state between the torsion prevention unit and the first and second main bodies may be provided to maintain the structural strength and the firm coupling force to the torsion stress, thereby previously preventing the fatal problems such as the breakage due to the torsion from occurring when compared to the cage according to the related art.

Also, according to the present invention, the first spacing protrusion piece may be provided at the rear side of the bottom surface of the first main body, the second spacing protrusion piece may be provided at the rear side of the top surface of the second main body, and the first and second spacing protrusion pieces may be inserted between the first vertebra and the second vertebra adjacent to the first vertebra in the state in which the first and second spacing protrusion pieces contact each other to form the inclination that is gradually narrowed forward from the rear side on the whole. Thus, when compared to the cage according to the related art, the inserted front end of the cage according to the present invention may have the sharp shape to minimize the damage of the surrounding tissues such as blood vessels or nerves when the cage is inserted through the opening of the subject person.

Also, according to the present invention, the autogenous bone chip or the artificial material substituting for the bone may be filled into the first and second main bodies to help the quick synostosis and osteoanagenesis.

Particularly, since the present invention is capable of being applied to surgical methods such as an oblique lateral interbody fusion (OLIF) method and a direct lateral interbody fusion (DLIF) method in addition to the well-known surgical methods such as the anterior lumbar interbody fusion (ALIF) method in which the cage is inserted from the front side of the vertebra after the abdominal operation, the lateral lumber interbody fusion (LLIF) method in which the cage is inserted through the side portion, the transforaminal lumbar interbody fusion (TLIF) method in which the cage is inserted in the diagonal direction at the point that is spaced a distance of 30 mm to 40 mm laterally from the center of the back, and the posterior lumbar interbody fusion (PLIF) method in which the cage is inserted from the back.

BRIEF DESCRIPTION OF THE DRAWINGS

FIG. 1 is a perspective view illustrating an overall structure of a cage apparatus for minimal invasive surgery according to an embodiment of the present invention, wherein FIG. 1(a) is a view when viewed from a rear side of first and second main bodies that are main parts of the present invention, and FIG. 1(b) is a view when viewed from a front side of the first and second main bodies that are main parts of the present invention.

FIGS. 3 to 6 are views sequentially illustrating a process of performing a surgical procedure by using the cage apparatus for the minimal invasive surgery according to an embodiment of the present invention, wherein FIG. 3 is an exploded perspective view illustrating a state before a torsion prevention unit is injected in a state in which the first and second main bodies that are main parts of the cage apparatus for the minimal invasive surgery are fixed to each other by using a front band and a rear band according to an embodiment of the present invention, FIG. 4 is a lateral exploded conceptual view when the state of FIG. 3 is viewed from a lateral side, FIG. 5 is a perspective view illustrating a state before a locking unit is coupled to the torsion prevention unit in the state in which the torsion prevention unit that is a main part of the cage apparatus for the minimal invasive surgery is coupled between the first and second main bodies according to the present invention, and FIG. 6 is a perspective view illustrating a state after the locking unit is coupled to the torsion prevention unit in the state in which the torsion prevention unit that is a main part of the cage apparatus for the minimal invasive surgery is coupled between the first and second main bodies according to the present invention.

FIG. 7 is a schematic conceptual view illustrating a process of performing a surgical procedure by using the cage apparatus for the minimal invasive surgery through a direct lateral interbody fusion (DLIF) method according to an embodiment of the present invention, wherein FIG. 7(a) is a plan conceptual view when a first vertebra and a second vertebra that is adjacent to the first vertebra are viewed from an upper side, and FIG. 7(b) is a perspective view illustrating a state in which the torsion prevention unit between the first and second main bodies is inserted between the first vertebra and the second vertebra through the side.

FIG. 8 is a schematic conceptual view illustrating a process of performing a surgical procedure by using the cage apparatus for the minimal invasive surgery through an oblique lateral interbody fusion (OLIF) method according to an embodiment of the present invention, wherein FIG. 8(a) is a plan conceptual view when the second vertebra is viewed from the upper side, and FIG. 8(b) is a perspective view illustrating a state in which the torsion prevention unit between the first and second main bodies is obliquely inserted between the first vertebra and the second vertebra from the side through a front side of an abdomen.

MODE FOR CARRYING OUT THE INVENTION

Figure 1:
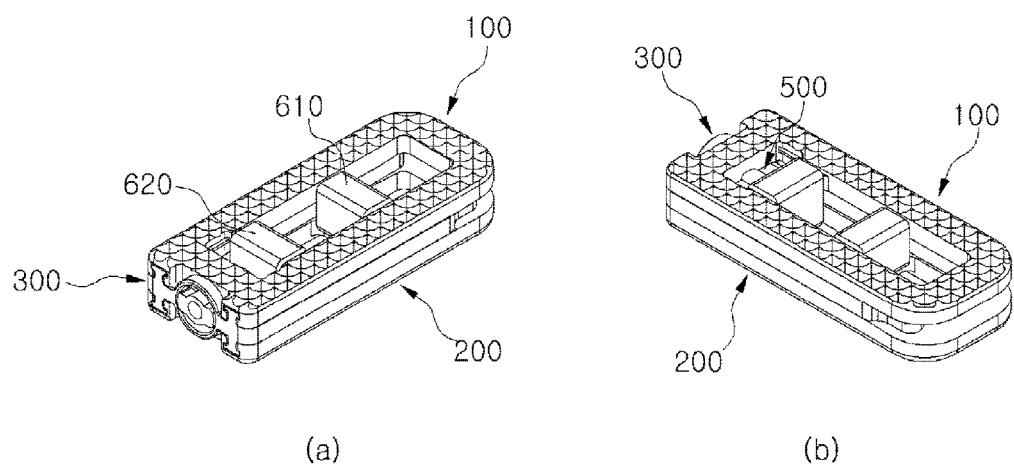

Advantages and features of the present disclosure, and implementation methods thereof will be clarified through following embodiments described with reference to the accompanying drawings.

The present invention may, however, be embodied in different forms and should not be construed as limited to the embodiments set forth herein.

In this specification, these embodiments are provided so that this disclosure will be thorough and complete, and will fully convey the scope of the present invention to those skilled in the art.

Also, the present invention is only defined by scopes of claims.

Accordingly, in some embodiments, well-known components, well-known device operations, and well-known techniques will not be described in detail to avoid ambiguous interpretation of the present invention.

Also, like reference numerals refer to like elements throughout. In the following description, the technical terms are used (mentioned) only for explaining a specific exemplary embodiment while not limiting the present disclosure.

The terms of a singular form may include plural forms unless referred to the contrary. The meaning of "include," "comprise," "including," or "comprising," specifies a component and an operation but does not exclude other components and operations.

Unless terms used in the present disclosure are defined differently, all terms (including technical and scientific terms) used herein have the same meaning as generally understood by those skilled in the art.

Also, unless defined apparently in the description, the terms are not ideally or excessively construed as having formal meaning.

Hereinafter, preferred embodiments of the present invention will be described in more detail with reference to the accompanying drawings.

For reference, FIG. 1 is a perspective view illustrating an overall structure of a cage apparatus for minimal invasive surgery according to an embodiment of the present invention, wherein FIG. 1(a) is a view when viewed from a rear side of first and second main bodies 100 and 200 that are main parts of the present invention, and FIG. 1(b) is a view when viewed from a front side of the first and second main bodies 100 and 200 that are main parts of the present invention.

Figure 2:
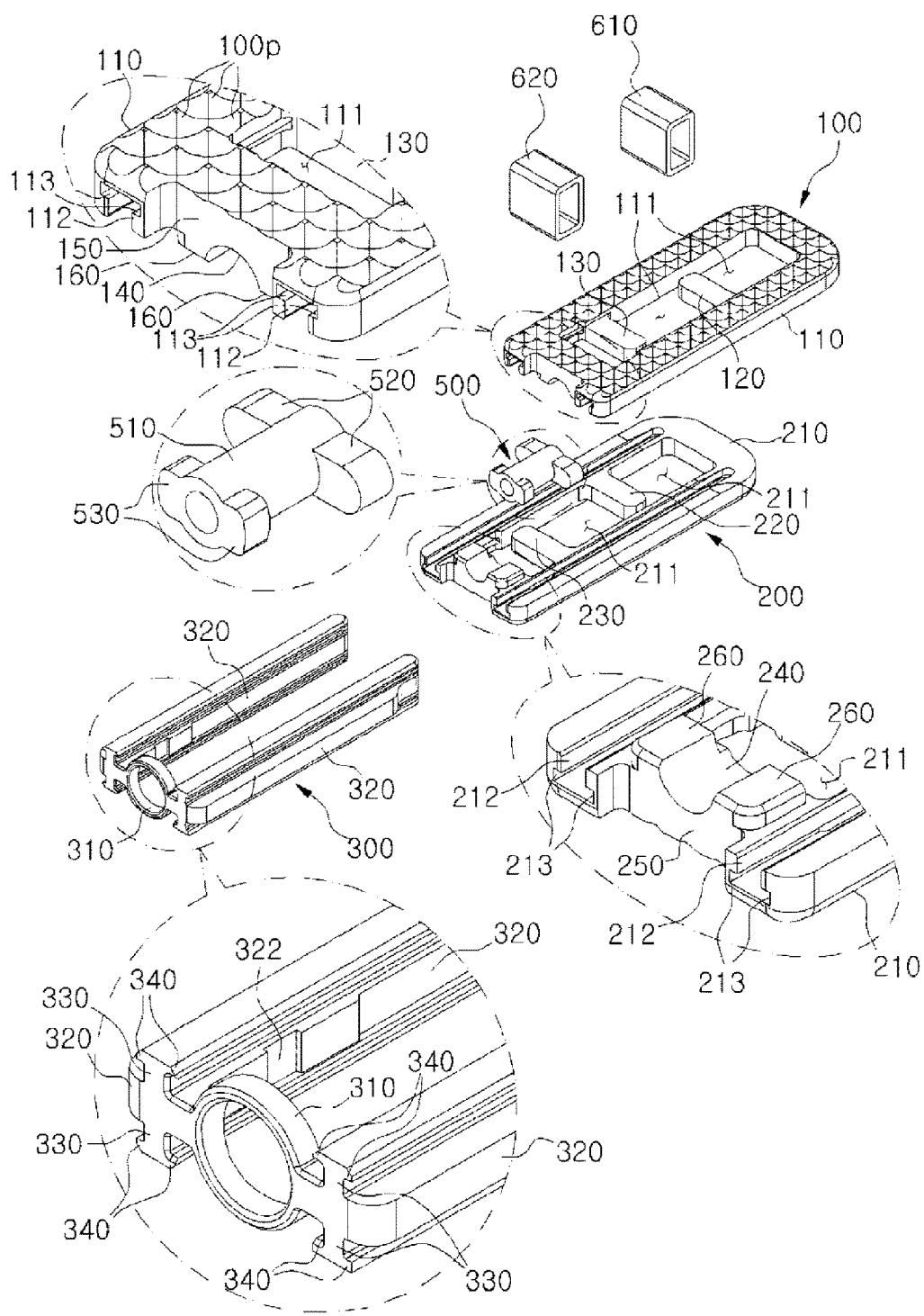
FIG. 2 is an exploded perspective view illustrating the overall structure of the cage apparatus for the minimal invasive surgery according to an embodiment of the present invention.

FIG. 2 is an exploded perspective view illustrating the overall structure of the cage apparatus for the minimal invasive surgery according to an embodiment of the present invention.

First, as illustrated in the drawings, it is seen that the present invention has a structure in which a torsion prevention unit 300 is coupled between the first and second main bodies 100 and 200, and a coupling state between a locking unit 500 and the torsion prevention unit 300 is capable of being maintained or released.

Figure 7:
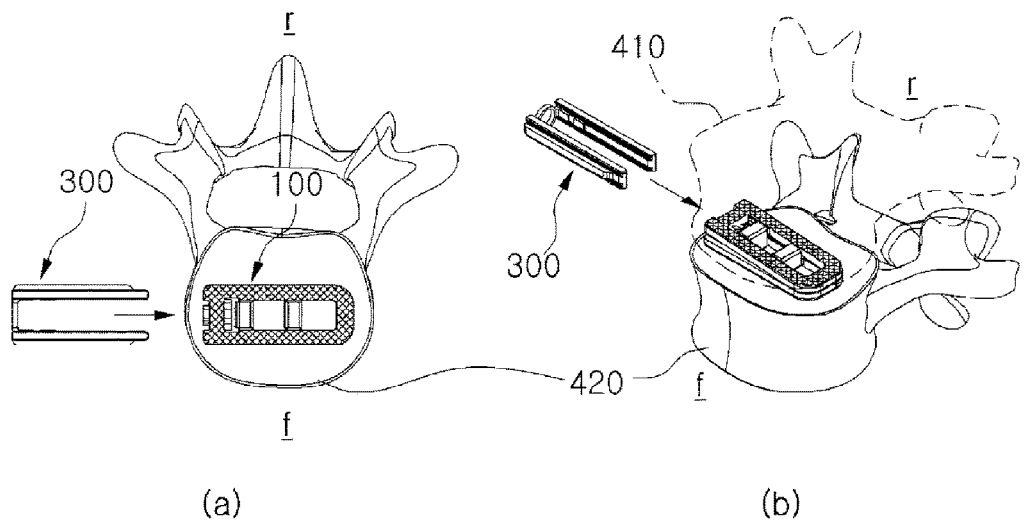
Figure 8:
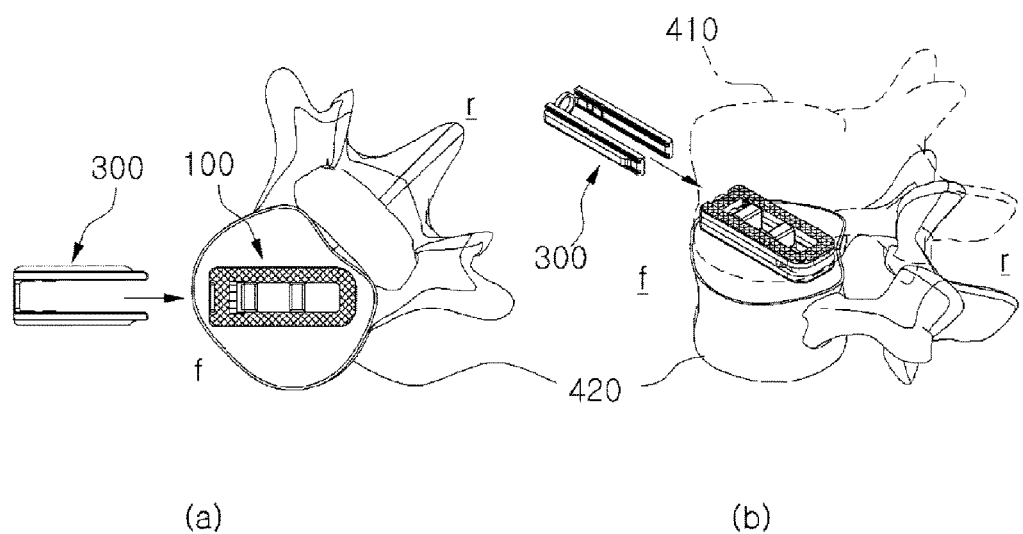

The first main body 100 is inserted between a first vertebra 410 (refer to FIGS. 7(b) and 8(b)) and a second vertebra 420 (refer to FIGS. 7 and 8).

The second main body 200 is inserted between the first vertebra 410 and the second vertebra 420 to face the first main body 100.

The torsion prevention unit 300 is fixed to both edges of each of the first and second main bodies 100 and 200 and disposed between the first and second main bodies 100 and 200.

The locking unit 500 is forwardly/reversely rotatably mounted between the first and second main bodies 100 and 200 and suppresses movement of the torsion prevention unit 300 between the first and second main bodies 100 and 200.

Thus, according to the present invention, a structure in which the torsion prevention unit 300 is coupled between the first and second main bodies 100 and 200, and the locking unit 500 maintains the coupled state between the torsion prevention unit 300 and the first and second main bodies 100 and 200 may be provided to maintain structural strength and firm coupling force to the torsion stress, thereby previously preventing fatal problems such as breakage due to torsion from occurring when compared to a cage according to the related art.

The foregoing embodiment as well as following various embodiments may be applied to the present invention.

First, the present invention may further include a plurality of protrusions 100p and 200p (refer to FIGS. 2 and 4) on a top surface of the first main body 100 and a bottom surface of the second main body 200 to maintain a state in which the first and second main bodies 100 and 200 are securely firmly attached and fixed between the first vertebra 410 and the second vertebra 420 and a state in which the mutually fixed state between the first and second main bodies 100 and 200 due to synostosis and osteoanagenesis.

An embodiment in which first spacing protrusion pieces 160 protruding from both rear sides of the bottom surface of the first main body 100 and second spacing protrusion pieces 260 protruding from both rear sides of the top surface of the second main body 200 to contact the first spacing protrusion pieces 160 are further provided may be applied to the present invention.

Figure 3:
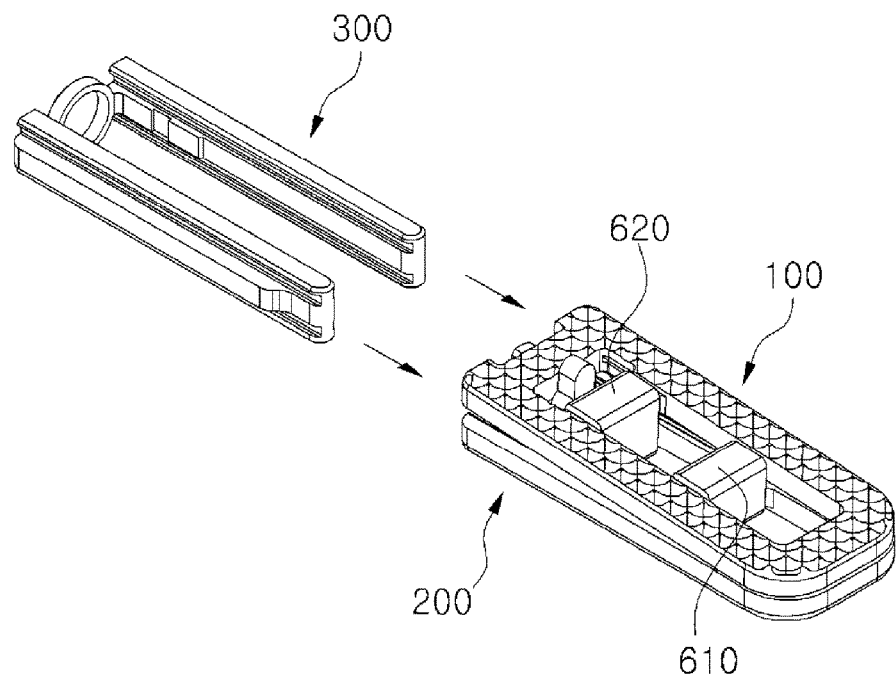
Figure 4:
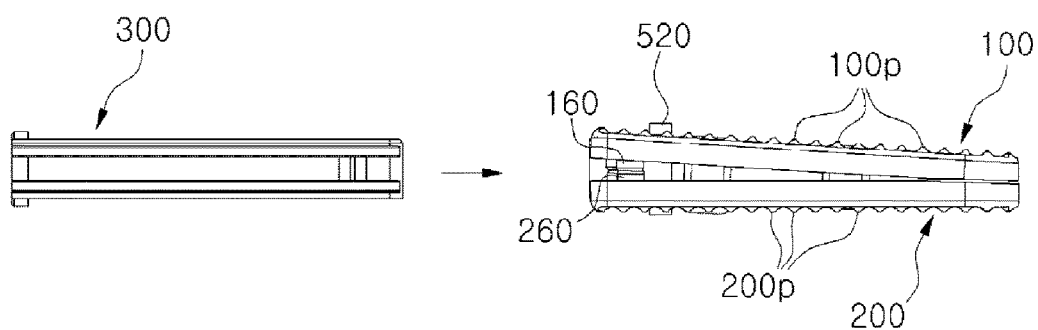

Thus, in a state in which the first spacing protrusion pieces 160 and the second spacing protrusion pieces 260 contact each other to form an inclination that is gradually narrowed forward from the rear side of each of the first and second main bodies 100 and 200 as illustrated in FIGS. 3 and 4, a front end of the torsion prevention unit 300 may be guided between the rear side of the bottom surface of the first main body 100 and the rear side of the top surface of the second main body 200 and then be inserted and coupled.

That is, according to the present invention, since the inserted front end of each of the first and second main bodies 100 and 200 has a relatively sharp shape when compared to that of a cage according to the related art, damage such as surrounding tissues such as blood vessels or nerves may be minimized when the cage is inserted through an opening of a subject person.

In more detail with reference to FIG. 2, it is seen that the first main body 100 has a following structure.

First, a first operation through-hole 111 having a predetermined length and width is formed in the first main body 100, and the first main body 100 includes a first outer frame 110 having four sides.

Also, the first main body 100 includes a first front hook rib 120 protruding from a right edge of the first operation through-hole 111 in a left direction.

Also, the first main body 100 includes a first rear hook rib 130 protruding from a left edge of the first operation through-hole 111 in a right direction and disposed at a rear side of the first front hook rib 120.

Also, the first main body 100 is provided on a rear end of the first outer frame 110 and disposed on a bottom surface of the first outer frame 110. The first main body 100 includes a first coupling groove 140 that is recessed in a circular arc shape and to which the locking unit 500 is coupled.

Also, the first main body 100 includes a first operation stepped groove 150 that is recessed from a side surface of the rear end of the first outer frame 110 to accommodate the rear end of the locking unit 500.

Here, it is seen that the bottom surface of the first outer frame 110 faces the top surface of the second main body 200 that will be described later, and both sides of the torsion prevention unit 300 are coupled to the left and right bottom surfaces of the first outer frame 110.

Here, it is preferable that each of both sides of the front end of the first outer frame 110 is rounded to be smoothly inserted through the opening of the subject person without causing friction with the surrounding tissues.

Also, it is seen that an end of the first front hook rib 120 faces a left surface of the first operation through-hole 111 and is adjacent to the left surface of the first operation through-hole 111, and an end of the first rear hook rib 130 faces a right surface of the first operation through-hole 111 and is adjacent to the right surface of the first operation through-hole 111.

In more detail, it is seen that the second main body 200 has a following structure.

First, a second operation through-hole 211 having a predetermined length and width is formed in the second main body 200, and the second main body 200 includes a second outer frame 210 having four sides.

Also, the second main body 200 includes a second front hook rib 220 protruding from a left edge of the second operation through hole 211 in a right direction.

Also, the second main body 200 includes a second rear hook rib 230 protruding from a right edge of the second operation through-hole 211 in a left direction and disposed at a rear side of the second front hook rib 220.

Also, the second main body 200 is provided on a rear end of the second outer frame 210 and disposed on a top surface of the second outer frame 210. The second main body 200 includes a second coupling groove 240 that is recessed in a circular arc shape and to which the locking unit 500 is coupled.

Also, the second main body 200 includes a second operation stepped groove 250 that is recessed from a side surface of the rear end of the second outer frame 210 to accommodate the rear end of the locking unit 500.

Here, it is seen that the top surface of the second outer frame 210 faces the bottom surface of the first main body 100, and both sides of the torsion prevention unit 300 are coupled to the top surface of both left and right sides of the second outer frame 210.

Here, it is preferable that each of both sides of the front end of the second outer frame 210 is rounded to be smoothly inserted through the opening of the subject person without causing friction with the surrounding tissues.

Also, it is seen that an end of the second front hook rib 220 faces a right surface of the second operation through-hole 211 and is adjacent to the right surface of the second operation through-hole 211, and an end of the second rear hook rib 230 faces a left surface of the second operation through-hole 211 and is adjacent to the left surface of the second operation through-hole 211.

Also, an autogenous bone chip or an artificial material substituting for the bone may be filled into each of the first and second operation through-holes 111 and 211 the first and second main bodies 100 and 200 to help quick synostosis and osteoanagenesis.

In more detail, it is seen that the torsion prevention unit 300 has a following structure.

First, the torsion prevention unit 300 includes a protection guide ring 310 having a ring shape and into which the first operation stepped groove 150 defined to be recessed in a rear outer surface of the first main body 100 and the second operation stepped groove 250 defined to be recessed in a rear outer surface of the second main body 200 are accommodated.

Also, the torsion prevention unit 300 includes a pair of coupling ribs 320 respectively extending from both sides of an outer circumferential surface of the protection guide ring 310 in parallel to each other and coupled to the left and right bottom surfaces of the first main body 100 and the left and right top surfaces of the second main body 200.

Also, the torsion prevention unit 300 includes main guide ribs 330 respectively extending in the formation directions of the pair of coupling ribs 320 to respectively protrude from the top and bottom surfaces of the pair of coupling ribs 320.

Also, the torsion prevention unit 300 includes auxiliary guide protrusion pieces 340 respectively protruding from both ends of the main guide ribs 330 in the formation directions of the main guide ribs 330.

Here, the rear end of the locking unit 500 that will be described later is forwardly/reversely rotatably accommodated into an inner space of the protection guide ring 310, and the front end of the locking unit 500 is detachably coupled to inner surfaces of the pair of coupling ribs 320 facing each other.

Here, a coupling structure having a shape corresponding to that of each of the main guide ribs 330 and the auxiliary guide protrusion pieces 340 is disposed on each of the left and right bottom surfaces of the first main body 100 and the left and right top surfaces of the second main body 200.

Also, torsion prevention unit 300 further includes a detachment groove 322 disposed on each of the inner surfaces of the pair of coupling ribs 320 and to which detachable wings 520 respectively disposed on both sides of the front end of the locking unit 500 are detachably coupled so as to be securely detached from and coupled to the locking unit 500 that will be described later.

In more detail, it is seen that the locking unit 500 has a following structure.

First, the locking unit 500 includes a rotatable body 510 having a cylindrical shape and of which an outer circumferential surface contacts the first coupling groove 140 defined in the rear bottom surface of the first main body 100 and the second coupling groove 240 defined in the rear top surface of the second main body 200 so as to be forwardly/reversely rotatably coupled.

Also, the locking unit 500 includes detachable wings 520 detachably coupled to the left and right inner surfaces of the torsion prevention unit 300 that is coupled and disposed between the first and second main bodies 100 and 200 while respectively extending from both sides of an outer circumferential surface of a front end of the rotatable body 510 and being interlocked with the rotatable body 510 so as to be forwardly/reversely rotated.

Also, the locking unit 500 includes control wings 530 that maintain or release the coupled state of each of the detachable wings 520 with respect to the torsion prevention unit 300 while respectively extending from both sides of an outer circumferential surface of a rear end of the rotatable body 510 and being interlocked with the rotatable body 510 so as to be forwardly/reversely rotated.

Figure 5:
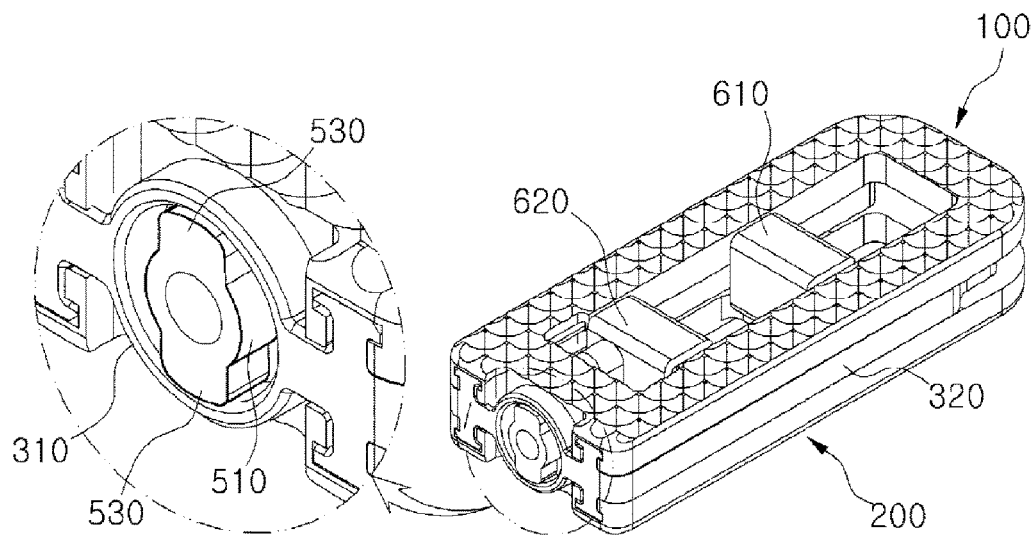
Figure 6:
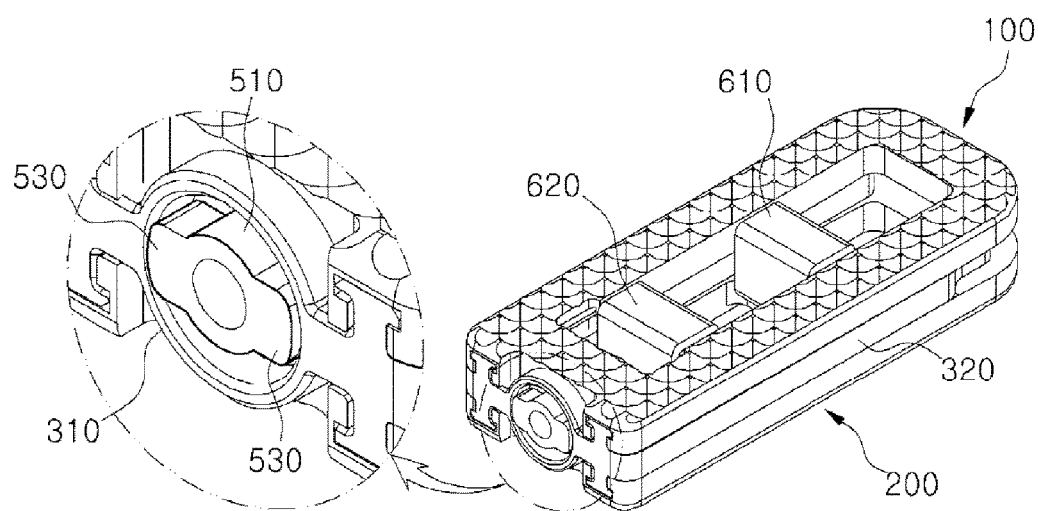

Here, the control wings 530 are forwardly/reversely rotatably accommodated into an inner space of the protection guide ring 310 as illustrated in FIGS. 5 and 6.

Thus, the control wings 530 as separate operation tools each of which has a groove having a shape corresponding to that of each of the control wings 530 may be forwardly/reversely rotated to convert a separable state of the detachable wings 520 from the detachment groove 322 as illustrated in FIG. 5 into a fixed state of the detachable wings 520 to the detachment groove 322 as illustrated in FIG. 6.

The present invention may further include a front band 610 and a rear band 620 to realize a primarily fixed state between the first and second main bodies 100 and 200 without interfering in slidable coupling of the pair coupling ribs 320 of the torsion prevention unit 300 between the first and second main bodies 100 and 200.

The front band 610 may fix the first front hook rib 120 disposed on the front side of the first main body 100 and the second front hook rib 220 disposed on the front side of the second main body 200 to mutually face-to-face contact the first front hook rib 120 at the same time. The front band 610 may be made of an elastic material such as medical rubber.

The rear band 620 may fix the first rear hook rib 130 disposed on the rear side of the first main body 100 and the second rear hook rib 230 disposed on the rear side of the second main body 200 to mutually face-to-face contact the first rear hook rib 130 at the same time. The rear band 620 may be made of an elastic material such as medical rubber.

A mutual coupling relationship between the first and second main bodies 100 and 200 and the front and rear bands 610 and 620 will be described in more detail.

That is, the front band 610 is inserted from an end of the first front hook rib 120 to fix the front side of the second main body 200 together with the first outer frame 110 at the same time.

That is to say, the front band 610 is inserted from an end of the second front hook rib 220 to fix the front side of the first main body 100 together with the second outer frame 210 at the same time.

Also, the rear band 620 is inserted from the end of the first front hook rib 130 to fix the rear side of the second main body 200 together with the first outer frame 110 at the same time.

That is to say, the rear band 620 is inserted from the end of the second front hook rib 230 to fix the rear side of the first main body 100 together with the second outer frame 210 at the same time.

A mutual coupling relationship between the first and second main bodies 100 and 200 and the torsion prevention unit 300 will be described in more detail.

First, the first main body 100 may further include a first main guide rail 112 having a predetermined length and recessed upward along each of left and right bottom surfaces of the first outer frame 110 and first auxiliary guide grooves 113 recessed in both upper sides in the formation direction of the first main guide rail 112.

Thus, the torsion prevention unit 300 has both side portions having shapes corresponding to those of the first main guide rail 112 and the first auxiliary guide grooves 113, i.e., includes the main guide ribs 330 and the auxiliary guide protrusion pieces 340.

That is, the first main guide rail 112 and the first auxiliary guide grooves 113 may have an 'H'-shaped cross-section on the whole together with a second main guide rail 212 and second auxiliary guide grooves 213 of the second main body 200, which will be described later.

Thus, the first main guide rail 112 and the first auxiliary guide grooves 113 may guide the slidable coupling of the torsion prevention unit 300. Also, the first main guide rail 112 and the first auxiliary guide grooves 113 have durability against the torsion stress when the coupling is completed to maintain structural strength against deformation such as torsion.

Also, the second main body 200 may further include a second main guide rail 212 having a predetermined length and recessed upward along each of left and right top surfaces of the second outer frame 210 and second auxiliary guide grooves 213 recessed in both lower sides in the formation direction of the second main guide rail 212.

Thus, the torsion prevention unit 300 has both side portions having shapes corresponding to those of the second main guide rail 212 and the second auxiliary guide grooves 213, i.e., includes the main guide ribs 330 and the auxiliary guide protrusion pieces 340.

That is, the second main guide rail 212 and the second auxiliary guide grooves 213 may have an 'H'-shaped cross-section on the whole together with the first main guide rail 112 and the first auxiliary guide grooves 113 of the first main body 100.

Thus, the second main guide rail 212 and the second auxiliary guide grooves 213 may guide the slidable coupling of the torsion prevention unit 300. Also, the second main guide rail 212 and the second auxiliary guide grooves 213 have durability against the torsion stress when the coupling is completed to maintain structural strength against deformation such as torsion.

A mutual coupling relationship between the first and second main bodies 100 and 200, the torsion prevention unit 300, and the locking unit 500 will be described in more detail.

First, the rotatable body 510 of the locking unit 500 is forwardly/reversely rotatably coupled inside the second main body 200 by contacting an outer circumferential surface of the first coupling groove 140.

Also, the rotatable body 510 is forwardly/reversely rotatably coupled inside the first main body 100 by contacting an outer circumferential surface of the second coupling groove 240.

Also, the detachable wings 520 are detachably coupled to the left and right inner surfaces of the torsion prevention unit 300 that is coupled and disposed between the first outer frame 110 and the second main body 200 while respectively extending from both sides of the outer circumferential surface of the front end of the rotatable body 510 and being interlocked with the rotatable body 510 so as to be forwardly/reversely rotated.

Also, the detachable wings 520 are detachably coupled to the left and right inner surfaces of the torsion prevention unit 300 that is coupled and disposed between the second outer frame 210 and the first main body 100 while respectively extending from both sides of the outer circumferential surface of the front end of the rotatable body 510 and being interlocked with the rotatable body 510 so as to be forwardly/reversely rotated.

The control wings 530 maintain or release the coupled state of each of the detachable wings 520 with respect to the torsion prevention unit 300 while respectively extending from both sides of the outer circumferential surface of the rear end of the rotatable body 510 and being interlocked with the rotatable body 510 so as to be forwardly/reversely rotated.

The control wings 530 maintain or release the coupled state of each of the detachable wings 520 with respect to the torsion prevention unit 300 while respectively extending from both sides of the outer circumferential surface of the rear end of the rotatable body 510 and being interlocked with the rotatable body 510 so as to be forwardly/reversely rotated.

First, in the state in which the first and second main bodies 100 and 200 are inserted between the first vertebra 410 and the second vertebra 420, the control wings 530 are disposed in a direction perpendicular to the first and second main bodies 100 and 200 as illustrated in FIG. 5. This arrangement may be in a state in which the coupling ribs 320 of the torsion prevention unit 300 are separable from the first and second main bodies 100 and 200.

Thereafter, when the control wings 530 are rotated as illustrated in FIG. 6, the detachable wings 520 may be maintained to the state of being coupled and fixed to the first and second main bodies 100 and 200.

A process of performing a surgical procedure by using the cage apparatus for the minimal invasive surgery according to various embodiments of the present invention will be described with reference to FIGS. 3 to 6.

For reference, FIGS. 3 to 6 are views sequentially illustrating the process of performing the surgical procedure by using the cage apparatus for the minimal invasive surgery according to an embodiment of the present invention.

For reference, non-explained reference numeral in FIGS. 3 to 6 will refer to FIGS. 1 and 2.

First, FIG. 3 is an exploded perspective view illustrating a state before the torsion prevention unit 300 is injected in a state in which the first and second main bodies 100 and 200 that are main parts of the cage apparatus for the minimal invasive surgery are fixed to each other by using the front band 610 and the rear band 620 according to an embodiment of the present invention.

Also, FIG. 4 is a lateral exploded conceptual view when the state of FIG. 3 is viewed from a lateral side.

Also, FIG. 5 is a perspective view illustrating a state before the locking unit 500 is coupled to the torsion prevention unit 300 in the state in which the torsion prevention unit 300 that is a main part of the cage apparatus for the minimal invasive surgery is coupled between the first and second main bodies 100 and 200 according to the present invention.

Also, FIG. 6 is a perspective view illustrating a state after the locking unit 500 is coupled to the torsion prevention unit 300 in the state in which the torsion prevention unit 300 that is a main part of the cage apparatus for the minimal invasive surgery is coupled between the first and second main bodies 100 and 200 according to the present invention.

First, as illustrated in FIGS. 3 and 4, the first and second main bodies 100 and 200 are disposed to overlap each other so that the first spacing protrusion pieces 160 and the second spacing protrusion pieces 260 face each other. Here, the front and rear sides of the first and second main bodies 100 and 200 are fixed by using the front and rear bands 610 and 620, and the detachable wings 520 and the control wings 530 of the locking unit 500 stand up in a direction perpendicular to the first and second main bodies 100 and 200.

Thereafter, the subject person moves the coupling ribs 320 of the torsion prevention unit 300 in an arrow direction of FIGS. 3 and 4 to allow the main guide ribs 330 and the auxiliary guide protrusion pieces 340, which protrude from the top and bottom surfaces of the coupling ribs 320, to be slidably moved in a state of being engaged with the first main guide rail 112 and the first auxiliary guide grooves 113 of the first main body 100 and the second main guide rail 212 and the second auxiliary guide grooves 213 of the second main body 200.

Here, the first and second main bodies 100 and 200 may have an inclination that is gradually narrowed forward the rear side as illustrated in FIG. 4 in the state in which the first spacing protrusion pieces 160 and the second spacing protrusion pieces 260 mutually face-to-face contact each other so that the first and second main bodies 100 and 200 are smoothly inserted between the first and second vertebrae 410 and 420.

Thereafter, in the state in which the torsion prevention unit 300 is coupled between the first and second main bodies 100 and 200 as illustrated in FIGS. 5 and 6, the subject person may rotate the control wings 530 that are in the arranged state of FIG. 5 to become the state of FIG. 6 by using a separate operation tool. Thus, the detachable wings 520 may be fixed to the detachment groove 322 of the torsion prevention unit 300.

As described above, the cage apparatus for the minimal invasive surgery according to an embodiment of the present invention may be applied to the surgical methods such as the direct lateral interbody fusion (DLIF) method of FIG. 7 and the oblique lateral interbody fusion (OLIF) method of FIG. 8 in addition to the ALIF, LLIF, TLIF, and PLIF methods, which are well-known.

For reference, FIG. 7 is a schematic conceptual view illustrating a process of performing a surgical procedure by using the cage apparatus for the minimal invasive surgery through the direct lateral interbody fusion (DLIF) method according to an embodiment of the present invention.

Here, FIG. 7(a) is a plan conceptual view when the first vertebra 410 and the second vertebra 420 that is adjacent to the first vertebra 410 are viewed from an upper side, and FIG. 7(b) is a perspective view illustrating a state in which the torsion prevention unit 300 between the first and second main bodies 100 and 200 is inserted between the first vertebra 410 and the second vertebra 420 through the side.

FIG. 8 is a schematic conceptual view illustrating a process of performing a surgical procedure by using the cage apparatus for the minimal invasive surgery through the oblique lateral interbody fusion (OLIF) method according to an embodiment of the present invention.

Here, FIG. 8(a) is a plan conceptual view when the second vertebra 420 is viewed from the upper side, and FIG. 8(b) is a perspective view illustrating a state in which the torsion prevention unit 300 between the first and second main bodies 100 and 200 is obliquely inserted between the first vertebra 410 and the second vertebra 420 from the side through a front side of an abdomen.

For reference, in FIGS. 7 and 8, reference symbol 'r' represents a back portion, i.e., a rear side of the subject person, and reference symbol 'f' represents an abdomen portion, i.e., a front side of the subject person.

That is, as illustrated in FIG. 7, a procedure for additionally inserting the torsion prevention unit 300 in the state in which the first and second main bodies 100 and 200 are inserted between the first vertebra 410 and the second vertebra 420 from the side of the subject person, i.e., the DLIF may be enabled.

Also, as illustrated in FIG. 8, a procedure for additionally inserting the torsion prevention unit 300 in the state in which the first and second main bodies 100 and 200 are obliquely inserted between the first vertebra 410 and the second vertebra 420 from the front side of the abdomen of the subject person, i.e., the OLIF may be enabled.

As described above, it is seen that the fundamental technical ideas of the present invention is to provide the cage apparatus for the minimal invasive surgery, which is capable being easily inserted between a vertebra and an adjacent vertebra during the surgery to previously prevent damage due to the torsion from occurring.

Also, it should be understood that numerous other modifications and embodiments can be devised by those skilled in the art that will fall within the spirit and scope of the principles of this disclosure.

100 . . . First main body
100p, 200p . . . Protrusion
110 . . . First outer frame
111 . . . First operation through-hole
112 . . . First main guide rail
113, 113 . . . First auxiliary guide groove
120 . . . First front hook rib
130 . . . First rear hook rib
140 . . . First coupling groove
150 . . . First operation stepped groove
160, 160 . . . First spacing protrusion piece
200 . . . Second main body
210 . . . Second outer frame
211 . . . Second operation through-hole
212 . . . Second main guide rail
213, 213 . . . Second auxiliary guide groove
220 . . . Second front hook rib
230 . . . Second rear hook rib
240 . . . Second coupling groove
250 . . . Second operation stepped groove
260, 260 . . . Second spacing protrusion piece
300 . . . Torsion prevention unit
310 . . . Protection guide ring
320, 320 . . . Pair of coupling ribs
322 . . . Detachment groove
330, 330 . . . Main guide rib
340, 340 . . . Auxiliary guide protrusion piece
410 . . . First vertebra
420 . . . Second vertebra
500 . . . Locking unit
510 . . . Rotatable body
520, 520 . . . Detachable wings
530, 530 . . . Control wings
610 . . . Front band
620 . . . Rear band

The invention claimed is:

1. A cage apparatus for a minimal invasive surgery, the cage apparatus comprising:
a first main body configured to be inserted between a first vertebra and a second vertebra adjacent to the first vertebra;
a second main body configured to be inserted between the first vertebra and the second vertebra to face the first main body;
a torsion prevention unit fixed to each of both edges of each of the first and second main bodies and disposed between the first and second main bodies; and
a locking unit forwardly/reversely rotatably mounted between the first and second main bodies to suppress movement of the torsion prevention unit between the first and second main bodies,
wherein the first main body comprises:
a first outer frame in which a first operation through-hole having a predetermined length and width is defined and having four sides;

a first front hook rib protruding from a right edge of the first operation through-hole in a left direction;
a first rear hook rib protruding from a left edge of the first operation through-hole in a right direction and disposed at a rear side of the first front hook rib;
a first coupling groove defined in a rear end of the first outer frame and disposed on a bottom surface of the first outer frame, the first coupling groove being recessed in a circular arc shape and coupled to the locking unit; and
a first operation stepped groove recessed from a side surface of the rear end of the first outer frame and into which a rear end of the locking unit is accommodated,
wherein the bottom surface of the first outer frame faces a top surface of the second main body, and
both sides of the torsion prevention unit are respectively coupled to left and right bottom surfaces of the first outer frame.

2. The cage apparatus of claim 1, further comprising:
a first spacing protrusion piece protruding from each of both sides of a rear bottom surface of the first main body; and
a second spacing protrusion piece protruding from each of both sides of a rear top surface of the second main body to contact the first spacing protrusion piece,
wherein, when the first and second spacing protrusion pieces contact each other to form an inclination that is gradually narrowed forward from a rear side of each of the first and second main bodies, a front end of the torsion prevention unit is guided to be inserted and coupled between the rear bottom surface of the first main body and the rear top surface of the second main body.

3. The cage apparatus of claim 1, wherein the torsion prevention unit comprises:
a protection guide ring having a ring shape and accommodated into each of the first operation stepped groove recessed from a rear outer surface of the first main body and a second operation stepped groove recessed from a rear outer surface of the second main body;
a pair of coupling ribs extending from both sides of an outer circumferential surface of the protection guide ring in parallel to each other and respectively coupled to left and right bottom surfaces of the first main body and left and right top surfaces of the second main body;
a main guide rib extending along a formation direction of each of the pair of coupling ribs to protrude from top and bottom surfaces of each of the pair of coupling ribs; and
an auxiliary guide protrusion piece protruding from each of both ends of the main guide rib along a formation direction of the main guide rib,
wherein a rear end of the locking unit is forwardly/reversely rotatably accommodated into an inner space of the protection guide ring, and
a front end of the locking unit is detachably coupled to inner surfaces of the pair of coupling ribs facing each other, and
a coupling structure having a space corresponding to that of each of the main guide rib and the auxiliary guide protrusion piece is disposed on each of the left and right bottom surfaces of the first main body and the left and right top surfaces of the second main body.

4. A cage apparatus for a minimal invasive surgery, the cage apparatus comprising:
a first main body configured to be inserted between a first vertebra and a second vertebra adjacent to the first vertebra;
a second main body configured to be inserted between the first vertebra and the second vertebra to face the first main body;
a torsion prevention unit fixed to each of both edges of each of the first and second main bodies and disposed between the first and second main bodies; and
a locking unit forwardly/reversely rotatably mounted between the first and second main bodies to suppress movement of the torsion prevention unit between the first and second main bodies,
wherein the second main body comprises:
a second outer frame in which a second operation through-hole having a predetermined length and width is defined and having four sides;
a second front hook rib protruding from a left edge of the second operation through-hole in a right direction;
a second rear hook rib protruding from a right edge of the second operation through-hole in a left direction and disposed at a rear side of the second front hook rib;
a second coupling groove defined in a rear end of the second outer frame and disposed on a top surface of the second outer frame, the second coupling groove being recessed in a circular arc shape and coupled to the lock unit; and
a second operation stepped groove recessed from a side surface of the rear end of the second outer frame and into which a rear end of the locking unit is accommodated,
wherein the top surface of the second outer frame faces a bottom surface of the first main body, and
both sides of the torsion prevention unit are respectively coupled to left and right top surfaces of the second outer frame.

5. A cage apparatus for a minimal invasive surgery, the cage apparatus comprising:
a first main body configured to be inserted between a first vertebra and a second vertebra adjacent to the first vertebra;
a second main body configured to be inserted between the first vertebra and the second vertebra to face the first main body;
a torsion prevention unit fixed to each of both edges of each of the first and second main bodies and disposed between the first and second main bodies; and
a locking unit forwardly/reversely rotatably mounted between the first and second main bodies to suppress movement of the torsion prevention unit between the first and second main bodies,
wherein the locking unit comprises:
a rotatable body having a cylindrical shape and forwardly/reversely rotatably disposed inside the first and second main bodies, an outer circumferential surface of the rotatable body contacting a first coupling groove defined in a rear bottom surface of the first main body and a second coupling groove defined in a rear top surface of the second main body;
detachable wings detachably coupled to left and right inner surfaces of the torsion prevention unit coupled and disposed between the first and second main bodies while respectively extending from both sides of an outer circumferential surface of a front end of the rotatable body and being interlocked with the rotatable body so as to be forwardly/backwardly rotatable; and control wings maintaining or releasing a coupled state of the detachable wings with respect to the torsion prevention unit while respectively extending from both sides of a rear end of the rotatable body and being interlocked with the rotatable body so as to be forwardly/backwardly rotatable.

6. A cage apparatus for minimal invasive surgery, the cage apparatus comprising:
   a first main body configured to be inserted between a first vertebra and a second vertebra adjacent to the first vertebra;
   a second main body configured to be inserted between the first vertebra and the second vertebra to face the first main body;
   a torsion prevention unit fixed to each of both edges of each of the first and second main bodies and disposed between the first and second main bodies;
   a locking unit forwardly/reversely rotatably mounted between the first and second main bodies to suppress movement of the torsion prevention unit between the first and second main bodies;
   a front band made of an elastic material and fixing a first front hook rib disposed on a front side of the first main body and a second front hook rib disposed on a front side of the second main body to contact each other; and
   a rear band made of an elastic material and fixing a first rear hook rib disposed on a rear side of the first main body and a second rear hook rib disposed on a rear side of the second main body to contact each other.

* * * * *